US00PP12266P2

(12) United States Plant Patent
Roberson

(10) Patent No.: US PP12,266 P2
(45) Date of Patent: Dec. 11, 2001

(54) LANTANA CAMARA PLANT NAMED 'ROBPATHOT'

(76) Inventor: Robert J. Roberson, 31706 E. Pink Hill Rd., Grain Valley, Jackson County, MO (US) 64029

( * ) Notice: Subject to any disclaimer, the term of this patent is extended or adjusted under 35 U.S.C. 154(b) by 0 days.

(21) Appl. No.: 09/350,381

(22) Filed: Jul. 1, 1999

(51) Int. Cl.[7] ..... A01H 5/00

(52) U.S. Cl. ..... Plt./227
(58) Field of Search ..... Plt./227

*Primary Examiner*—Bruce R. Campell
*Assistant Examiner*—June Hwu

(57) ABSTRACT

This invention relates to a new and distinct *Lantana camara* cultivar which is outstanding because of its: 1) bright fuschia colored floret clusters; 2) its reduced tendence to set seed; 3) its rapid growth rate (approximate mature size mound of 36"×36" in one growing season in USDA Zone 5); and 4) its mint-like aromatic foliage.

2 Drawing Sheets

SUMMARY OF THE INVENTION

This invention relates to a new and distinct *Lantana camara* cultivar which is outstanding because of its 1) bright fuschia colored floret clusters; 2) its reduced tendency to set seed; 3) its rapid growth rate (approximate mature size mound of 36"×36" in one growing season in USDA Zone 5); and 4) its mint-like aromatic foliage. The claimed *Lantana Camara* plant was primarily selected for these characteristics. This selection was made from a specially designed Lantana hydridizing program with said hybrid cultivars being planted and grown in Grain Valley, Mo.

ORIGIN AND ASEXUAL REPRODUCTION

Asexual reproduction of this cultivar by tip cuttings was directed by me, such reproduction establishing that the plant does in fact maintain the characteristics described, in successive generations.

It should be noted that the plant was initially selected from a Lantana planting being grown near Grain Valley, Mo. in a cultivated area and has since been reproduced by tip cuttings in the vicinity of Grain Valley, Mo. with the new and distinct characteristics stated herein, found to be maintained through successive generations as before recited.

*Lantana camara* is native to the subtropics and tropical North and South America. They are woody ornamentals which are not usually winter hardy North of USDA horticulture Zone 9. The roughish leaves range from yellow-green to green to blue-green and the two basic growth forms are mounding and trailing (weeping). Bloom color usually include yellow, white, cream, pink or orange.

The cultivar of *Lantana camara* 'Robpathot' may further be described as having a number of distinctive characteristics which are enumerated in the succeeding specific description but broadly stated as comprising; 1) bright fuschia colored floret clusters; 2) its reduced tendency to set seed; 3) its rapid growth rate (approximate mature size mound of 36"×36" in one growing season in USDA Zone 5); and 4) its mint-like aromatic foliage. I have chosen to identify this new cultivar as *Lantana camara* 'Ropathot'. This cultivar is being marketed in the United States under the name of Patriot™ Hot Country.

BRIEF DESCRIPTION OF THE DRAWING

The accompanying photographs show as nearly true as it is reasonably possible to make the same, in color illustrations of this character, typical leaves and flowers of the new variety. The photographic drawing illustrates the flower form and color and leaf color.

DETAILED DESCRIPTION

Figure 1:
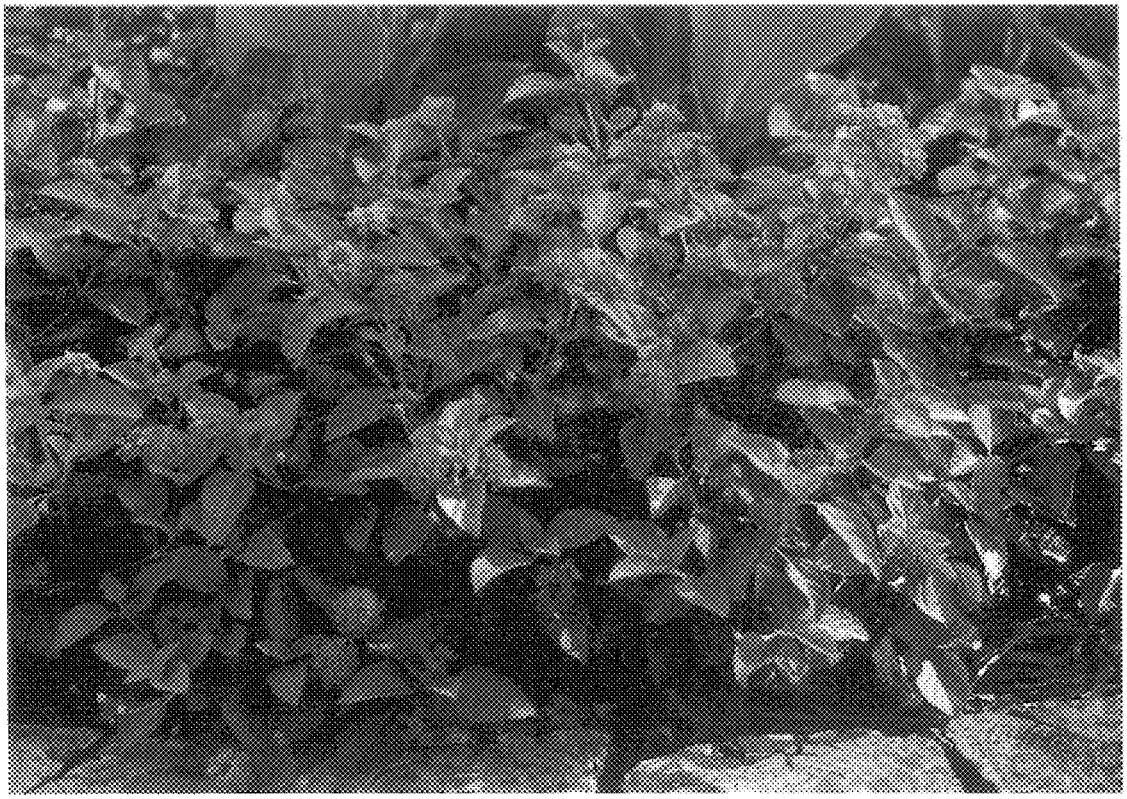
FIG. 1—illustrates the whole plant.
Figure 2:
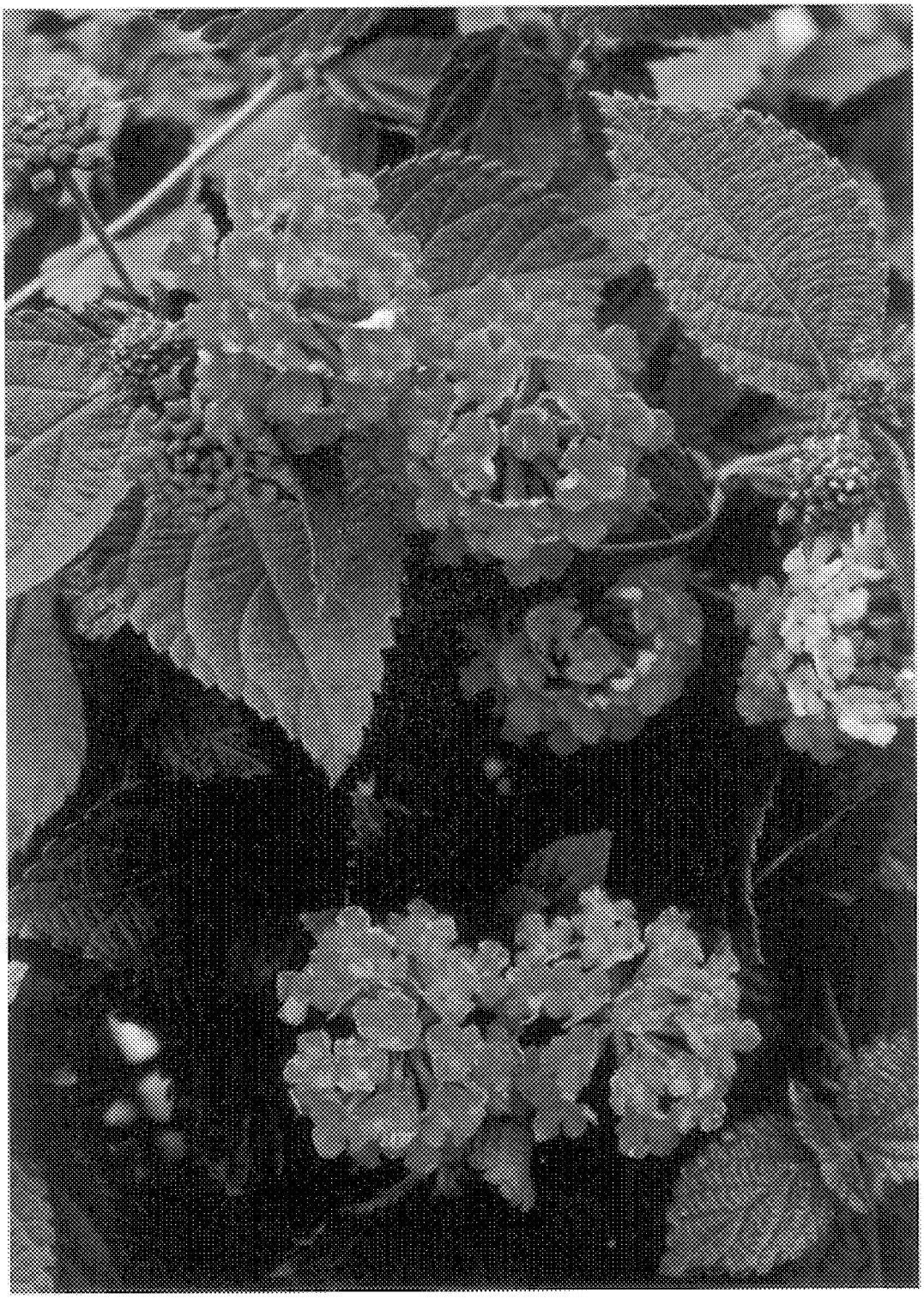
FIG. 2—illustrates the face view of the flower.

In order to more specifically identify the cultivar, descriptive details are set forth hereinafter, along with related aspects of the plant which serve to distinguish the same, all colors being noted as compared with the Pantone Matching System (PMS). The measurements and colors were recorded from mature plants grown in the vicinity of Grain Valley, Mo.

Parentage:

*Seed parent.*—*Lantana camera* 'Patriot™ Confetti' (not patented) in a semi-controlled open pollination.

*Pollen parent.*—Unknown.

Propagation: Asexual reproduction by tip cuttings started near Grain Valley, Mo.

Plant descriptions:

*Inflorescence and reproductive parts.*—The inflorescence is a flat topped round cluster of 25–30 florets. The individual clusters are determinate and arise from the leaf axils. Each individual floret is slightly un-symmetrical with a bilateral symmetry and is subtended by a single bract. The perianth consist of: the Calyx (5 united petals) and the Corolla (5 united petals with narrow tube). The flowers are zygomorphic, hermaphroditic, and have 4 introse stamens which are didynamous. The ovary is superior, the style is terminal, and the stigma is lobed. The ovary is 2 locular, but is divided into 4 loculi by a false septum in each loculus. The placentation is axile with 2 ovules per carpel. The fruit classification is drupe and potentially contains 2 seeds. When fruit forms, it is green (PMS #363); then matures through a deep purple (PMS #533) to a near black (PMS #532).

Inflorescence dimensions:
*Bloom cluster.*—1.5" in diameter.
*Single floret.*—0.4".
*Pedicle length.*—1.4".
*Corolla tube.*—0.5".

Inflorescence colors:
*Buds.*—Rich Fuschia.
*First opening.*—Yellow/sienna.
*Transitions.*—To mature Wine/fuschia.
*Transition time.*—24 hours (approximately).
*Tube.*—Lavender.

Developmental pattern: First flowers develop in a circular pattern on the periphery of the inflorescence.

Leaves and stems:
*Leaf shape.*—Ovate.
*Leaf margins.*—Serrate.
*Leaf tip and base.*—Acute.
*Leaf veins.*—Pinnate.
*Leaf surface.*—Rough due to bristly hairs.
*Leaf arrangement.*—Opposite.
*Leaf color.*—Immature leaves — deep green (PMS #363) maturing to a slightly darker forest green (PMS #364).
*Leaf size.*—Length 3.8". Petiole 0.7". Width 1.9".
*Stem.*—Square in youth becoming round and woody with age.

Roots: Highly branched and fibrous.

Flowering time: The color display begins blooming at 6–7 weeks after cuttings are made, or 4 weeks after potting, and continue until temperatures drop below 45 degrees Fahrenheit.

Diseases: No known diseases noted to date.

GENERAL OBSERVATIONS

*Lantana camara* 'Robpathot', with its 1) bright fushchia colored floret clusters; 2) its reduced tendency to set seed; 3) its rapid growth rate (approximate mature size mound of 36"×36" in one growing season in USDA Zone 5); and 4) its mint-like aromatic foliage.

For the purpose of ornamental horticulture in our present living environments which include smaller yards and patio gardening, *Lantana camara* plant "Robpathot" is ideal due to several characteristics:

A. It is an excellent plant for mass planted ground covers, low borders, hanging baskets or focal display containers. *Lantana camara* 'Robpathot' will produce a continuous display of bright, yellow/sienna quickly transitioning to wine/fuschia. This plant remains in bloom when most other flowering perennials' season has ended.
B. The prolific blooming tendency and dense growth habit of this cultivar, with its medium internode spaces provides the garden or landscape with a "fuller", more dense presentation of both foliage and bloom florets; thus making a more dramatic color statement than the average Lantana.
C. This cultivar's slow tendency to set seed allows more continual blooming, and a maintenance of optimum color beauty. This characteristic of being slow to set seed also provides the garden or landscape with a clean environment free of unwanted seedlings.
D. The ease of propagation of 'Robpathot' makes this Lantana a very commercially viable product to serve the horticulture industry.

COMPARISON TO KNOWN VARIETIES

*Lantana camara* plant 'Robpathot' should be compared with *Lantana camara* 'Robpatdes' (U.S. Plant Pat. No. 10,156). While similar, there are numerous differences between the claimed Lantana and 'Robpatdes' including the difference in floret colors. 'Robpatdes' has a multi-colored floret appearance because of the slower transition time while 'Robpathot' maintains an overall homogenous fushsia color.

I claim:

1. The new and distinct cultivar of *Lantana camara* plant substantially as illustrated and described.

* * * * *